United States Patent [19]

Smith et al.

[11] Patent Number: 4,569,794
[45] Date of Patent: Feb. 11, 1986

[54] PROCESS FOR PURIFYING PROTEINS AND COMPOUNDS USEFUL IN SUCH PROCESS

[75] Inventors: Michele C. Smith; Charles Pidgeon, both of Zionsville, Ind.

[73] Assignee: Eli Lilly and Company, Indianapolis, Ind.

[21] Appl. No.: 678,602

[22] Filed: Dec. 5, 1984

[51] Int. Cl.$^4$ .................................................. C07G 7/04
[52] U.S. Cl. ........................... 260/113; 260/112 R; 260/112.5 R; 260/112.5 LH; 260/112.5 S; 260/112.5 E; 260/112.7; 260/114; 260/115; 260/121
[58] Field of Search ............... 260/112 R, 112.5 S, 260/112.5 R, 113, 114, 115, 112.7, 121, 112.5 LH, 112.5 E

[56] References Cited

U.S. PATENT DOCUMENTS

| | | | |
|---|---|---|---|
| 3,959,249 | 5/1976 | Antonini | 260/121 X |
| 4,172,072 | 10/1979 | Ashmead | 260/115 |
| 4,216,143 | 8/1980 | Ashmead | 260/113 |
| 4,216,144 | 8/1980 | Ashmead | 260/115 |
| 4,472,509 | 9/1984 | Gansow et al. | 424/85 X |
| 4,476,116 | 10/1984 | Anik | 260/112.5 R X |

FOREIGN PATENT DOCUMENTS 2097279  11/1982  United Kingdom ............. 260/112.7

OTHER PUBLICATIONS

J. Biol. Chem. 253, 6908–6916 (1978), Miletich et al.
J. Biol. Chem. 253, 8980–8987 (1978), Furie et al.
J. Biol. Chem. 254, 9766–9771 (1979), Furie et al.
J. Biol. Chem. 255, 2790–2795 (1980), Tai et al.
J. Biol. Chem. 255, 8599–8605 (1980), Madar et al.
J. Biol. Chem. 257, 1836–1844 (1982), Madar et al.
Methods in Enzymology, 84, 60–83 (1982), Furie et al.
Biochemistry, 22, 948–954 (1983), Lewis et al.
Porath et al., *Nature* (London) 258, 598–599 (1975).
Lonnerdal et al., *J. Applied Biochemistry* 4, 203–208 (1982).
Porath et al., *Biochemistry* 22, 1621–1630 (1983).
Porath et al., *Affinity Chromatography and Biological Recognition,* Academic Press, Inc., 173–189 (1983).
Ortel et al., *Protides of the Biological Fluids,* vol. 30, Pergamon Press, New York, pp. 671–676 (1982).
Sulkowski et al., *Affinity Chromatography and Related Techniques,* Gribnau, T. C. J., Visser, J., and Nivard, R. J. F., Editors, Elsevier Scientific Publishing Co., Amsterdam (1982).

*Primary Examiner*—Howard E. Schain
*Attorney, Agent, or Firm*—William C. Martens; Arthur R. Whale

[57] ABSTRACT

This invention describes a process for separating a biologically active polypeptide or protein in the form of its precursor from a mixture containing said precursor and impurities, which comprises contacting said precursor with a resin containing immobilized metal ions, said precursor comprising the biologically active polypeptide or protein covalently linked directly or indirectly to an immobilized metal ion chelating peptide, binding said precursor to said resin, and selectively eluting said precursor from said resin. Such precursor compounds are also described.

27 Claims, No Drawings

PROCESS FOR PURIFYING PROTEINS AND COMPOUNDS USEFUL IN SUCH PROCESS

BACKGROUND OF THE INVENTION

In 1975, Porath introduced immobilized metal ion affinity chromatography (IMAC) for fractionating proteins [J. Porath, J. Carlsson, I. Olsson, and G. Belfrage, *Nature* (London) 258, 598-599 (1975)]. In Porath's work, IMAC consists of derivatizing a resin with iminodiacetic acid (IDA) and chelating metal ions to the IDA-derivatized resin. Proteins bind to the metal ions through unoccupied coordination sites and are immobilized on the column. Since then, workers have used ligands other than IDA to chelate metal ions to resins. Studies with serum proteins have shown IMAC to be an extremely specific and selective separation technique [J. Porath and B. Olin, *Biochemistry* 22, 1621-1630 (1983)].

It is recognized that certain amino acid residues such as histidine, cysteine, methionine, glutamic acid, aspartic acid, lysine, and tyrosine, present in metalloprotein active sites, are responsible, at least in part, for the actual binding of free metal ions to such apoproteins. The actual mechanisms which give rise to the binding of proteins to free metal ions are not well understood and are dependent upon a number of factors, not the least of which is the conformation of the particular protein. However, when the metal ions are immobilized, at least three additional limiting factors come into play, viz., reduced number of available coordination sites on the metal, restricted accessibility of the tethered metal to the binding sites on the protein, and, depending upon the characteristics of the resin, limited protein access to the immobilized metal ion. Thus, it is extremely difficult a priori to state which proteins will and which will not exhibit an affinity for immobilized metal ions.

Once binding has occurred, however, the protein can be released by protonation of its associated metal ion-binding ligand. Dissociation is achieved by lowering the pH of the surrounding buffer medium, a most common method for eluting bound proteins.

It has now been discovered that it is possible to apply the concept of immobilized metal ion affinity chromatography to the purification of a wide range of substances, and it is this discovery that forms the basis of the present invention. Thus, this invention is directed (1) to compounds specifically tailored so as to be readily purified via IMAC from mixtures containing such compounds and (2) to a process for such purification.

SUMMARY OF THE INVENTION

Thus, this invention is directed to a class of compounds comprising a biologically active polypeptide or protein covalently linked directly or indirectly to an immobilized metal ion chelating peptide.

Another embodiment of this invention is a process for separating a biologically active polypeptide or protein in the form of its precursor from a mixture containing said precursor and impurities, which comprises contacting said precursor with a resin containing immobilized metal ions, said precursor comprising the biologically active polypeptide or protein covalently linked directly or indirectly to an immobilized metal ion chelating peptide, binding said precursor to said resin, and selectively eluting said precursor from said resin.

DETAILED DESCRIPTION OF THE INVENTION

The advent of recombinant DNA methodology and therefore the availability of potentially unlimited quantities of polypeptides and proteins of diverse structure has brought about the need to develop methods for processing and purifying the resultant synthetic products. The process of this invention represents a response to this need, its focus being the purification of proteins and polypeptides, especially those which are recombinant DNA-sourced.

Thus, this invention involves a process for separating biologically active polypeptides and/or proteins from impurities. By the term "biologically active polypeptides and proteins" is meant polypeptides and proteins that are themselves biologically active or polypeptides and proteins that are useful in the production of biologically active polypeptides and proteins.

The polypeptides and proteins referred to herein can be naturally occurring or synthetic, and, if synthetic, can be produced by classical solution phase, by solid phase, or by recombinant DNA methodology. Preferably, the polypeptides and proteins contemplated herein are those produced via recombinant DNA methodology.

The compounds of this invention comprise two components, an aforedescribed biologically active polypeptide or protein and an immobilized metal ion chelating peptide directly or indirectly joined thereto by covalent bonding.

By the term "immobilized metal ion chelating peptide" as used herein is meant an amino acid sequence that chelates immobilized divalent metal ions of metals selected from the group consisting of cobalt, nickel, and copper.

Of the foregoing, metal ions preferred for chelation in the context of this invention are those from metals selected from the group consisting of nickel and copper. Of the two, nickel is more preferred.

The essential characteristics of the metal chelating peptide which is an element in the compounds of this invention are (1) that it chelates an immobilized metal ion and (2) that its chelating ability is maintained when attached to a biologically active polypeptide or protein. Many peptides will chelate metal ions under conditions in which both the ion and the peptide are free from external constraints. However, when the metal ion has been immobilized, its availability for chelation is much restricted and, moreover, when the peptide which exhibits chelating activity is also joined to another entity, i.e., a biologically active polypeptide or protein, the potential for chelation may be reduced. Thus, the chelating peptides that participate in the compositions of this invention carry both of the aforementioned properties.

Suitable preferred immobilized metal ion chelating peptides in accordance with this invention are those having at least one amino acid selected from the group consisting of histidine and cysteine. Most preferred immobilized metal ion chelating peptides are those containing histidine.

The optimal length of the immobilized metal ion chelating peptide in large part will be dependent upon the number of unoccupied coordination sites on the immobilized metal ion. Iminodiacetic acid, for example, through which the metal ion is bound to the resin, may be tridentate. Thus, depending upon the particular metal, as many as three vacant coordination sites are available on the metal ion bound to the resin via iminodiacetic acid. Selected dipeptides thus can serve as highly efficient tridentate ligands by providing at least three potential donor atoms. Normally, therefore, the chelating peptides contemplated herein will contain at least two and up to about five amino acids.

Examples of specific histidine-containing immobilized metal ion chelating peptides are those of the formula His-X in which X is selected from the group consisting of -Gly-His, -Tyr, -Gly, -Trp, -Val, -Leu, -Ser, -Lys, -Phe, -Met, -Ala, -Glu, -Ile, -Thr, -Asp, -Asn, -Gln, -Arg, -Cys, and -Pro.

A preferred sub-class of the foregoing is His-Trp, His-Tyr, His-Gly-His, and His-Phe, and, of these, His-Trp, His-Tyr, and His-Gly-His are most preferred.

Another class of histidine-containing immobilized metal ion chelating peptides is that defined by the formula Y-His in which Y preferably is Gly-, Ala-, or Tyr-.

Which immobilized metal ion chelating peptide is employed in any particular situation is, of course, dependent upon a number of factors, one of which is the identity of the metal ion. Thus, for example, if the metal ion is Ni(II), the following histidine-containing immobilized metal ion chelating peptides are preferred: His-Gly-His, His-Tyr, His-Trp, His-Gly, His-Val, His-Leu, His-Ser, His-Lys, His-Phe, His-Met, Gly-His, and Ala-His. If the metal ion is Cu(II), the following histidine-containing immobilized metal ion chelating peptides are preferred: His-Gly, His-Gly-His, His-Ala, His-Val, His-Leu, His-Ser, His-Glu, His-Lys, His-Phe, His-Tyr, His-Trp, and His-Met.

Compounds of this invention can be and preferably are prepared via recombinant DNA methodology. In their preparation, a nucleotide sequence coding for the desired polypeptide containing both the biologically active polypeptide or protein and the directly or indirectly linked chelating peptide is prepared using routine methods for such synthesis. These methods generally involve preparation of oligonucleotides coding both for fragments of the desired coding sequence and for the complementary sequence thereof. The oligonucleotides are designed to provide overlap of one fragment of the coding sequence with two fragments of the complementary sequence and vice versa. The oligonucleotides are paired and joined, ultimately producing the desired gene sequence.

The sequence is inserted into a cloning vector at a location which permits the peptide product for which it codes to be expressed. A suitable cloning vector contains at least a portion of a gene's expression control sequence.

A typical expression control sequence can be described in terms of five elements. In the order in which they appear in the gene, the elements are as follows: (a) the promoter region; (b) the 5' untranslated region; (c) the protein coding sequence; (d) the 3' untranslated region; and (e) the transcription termination site.

The function of each of these elements in gene systems is well recognized. The promoter region mediates initiation of messenger RNA (mRNA) production (transcription). The promoter may be (1) free of external control (constitutive), (2) under the control of a repressor, a substance that, when present, represses gene function, or (3) under the control of an inducer, a substance that is required to induce gene function. The lipoprotein (lpp) gene, for example, is free from external control and thus is termed "constitutive".

Located at or near the promoter is the "transcription initiation site", a point at which RNA polymerase binds to initiate DNA transcription. Once transcription is initiated, mRNA is produced. The structure of the resulting mRNA is determined by the DNA sequences of the gene elements (b), (c), and (d) above.

The resulting mRNA carries a sequence which is translatable into protein product. The translatable sequence is located downstream from the 5' untranslated region and upstream from the 3' untranslated region. Translation is mediated by the binding of ribosomes to a sequence in the mRNA 5' untranslated region denoted as the ribosome binding site and is initiated at the translation start codon (AUG) appearing as the first codon of the product gene sequence and coding as well for the amino acid methionine (Met). Translation terminates at one or more termination codons appearing at the end of the translation region.

By the techniques of recombinant DNA, it has become possible to prepare cloning vectors useful for the production of selected foreign (exogenous) proteins by inserting into such vectors an expression control sequence, i.e., a sequence of nucleotides that controls and regulates expression of structural genes with production of exogenous protein when operatively linked to those genes.

In the context of the foregoing, the term "expression control sequence" includes elements (a), (b), (d), and (e) above.

Recombinant DNA methodology can be employed to express compounds of this invention either as a portion of a larger "hybrid" molecule or by direct expression. In the direct expression mode, the cloning vector is designed such that the expression product is composed entirely of desired product preceded by a methionine (Met) residue resulting from the presence of the essential start codon. The superfluous Met residue can be removed by treating the product with cyanogen bromide or with phenyl isothiocyanate followed by a strong anhydrous acid, such as trifluoroacetic acid.

In the hybrid molecule expression mode, a DNA sequence coding for the desired product is inserted into the expression control sequence of a cloning vector at a point such that the product expressed comprises a hybrid protein. By "hybrid protein" as used herein is meant a recombinant DNA product comprising a foreign protein, generally all or a portion of the natural (endogenous) protein produced by the expression control sequence (for example, lipoprotein in the lipoprotein gene), to which is attached the desired protein, i.e., a compound of this invention.

The properly designed hybrid protein produced by recombinant DNA methodology will contain a cleavage site at the junction of the endogenous protein portion and the desired product. The cleavage site permits generation of mature product by chemical or enzymatic treatment of the hybrid protein product. Highly useful selective cleavage sites comprise a DNA sequence which codes for an amino acid or a sequence of amino acids which can be cleaved chemically or enzymatically at its C-terminal.

Examples of chemical agents useful for cleaving proteins are cyanogen bromide, 2-(2-nitrophenylsulfenyl)-3-bromo-3'-methylindolinium (BNPS-skatole), hydroxylamine, and the like. Cyanogen bromide cleaves proteins at the C-terminal of a methionine residue. Therefore, the selective cleavage site is a methionine residue itself.

Hydroxylamine cleaves at the C-terminal of the moiety -Asn-Z- in which Z is Gly, Leu, or Ala.

BNPS-skatole cleaves at the C-terminal of a tryptophan residue.

Examples of enzymatic agents useful for cleavage are trypsin, papain, pepsin, plasmin, thrombin, enterokinase, and the like. Each effects cleavage at a particular amino acid sequence which it recognizes. Enterokinase, for example, recognizes the amino acid sequence -(Asp)$_n$-Lys- in which n is an integer from 2 to 4.

The most preferred selective cleavage site, especially if the compounds of this invention lack methionine, is a methionine residue. This residue, joined to the N-terminus of the desired product, is readily cleaved by known methods using cyanogen bromide to produce the desired product, a compound of this invention.

In constructing useful cloning vectors, several elements are required. Two of the required elements are common to all useful cloning vectors. First, the vector must have a DNA segment containing a functional origin of replication (replicon). Plasmids and phage DNA by their very nature contain replicons facilitating replication in a host cell.

Secondly, the vector must have a DNA segment which conveys to a transformable host cell a property useful for selection of transformed cells from non-transformed cells. Any of a wide range of properties can be used for selection purposes. One of the most commonly used properties is antibiotic resistance, e.g., tetracycline resistance or ampicillin resistance.

The foregoing two elements generally are present in readily available and recognized cloning vectors. Examples of suitable cloning vectors are bacterial plasmids, such as plasmids from *E. coli*, including pBR322, pMB9, ColE1, pCR1; wider host range plasmids, including RP4; phage DNAs, such as lambda, and the like. Most, if not all, of the above recognized vectors already carry the aforedescribed two elements.

A third element is the expression control sequence. Any of a wide range of such control sequences can be used including, for example, those from the lipoprotein gene, the β-galactosidase gene, the tryptophan gene, the β-lactamase gene, phage lambda, and the like.

In producing a suitable cloning vector by insertion of the selected expression control sequence, routine methods are used. Various sites exist within cloning vectors at which cuts can be made using a restriction endonuclease specific for such site. Any of these sites can be selected for insertion of the expression control sequence. As an example, in the well-recognized and documented plasmid pBR322, several suitable restriction sites exist, any of which may be employed as insertion sites. A PstI site is located within the gene for β-lactamase. Other sites outside of any specific coding region are EcoRI and PvuII. These and other sites are well recognized by those skilled in the art.

Taking advantage of any of these sites or others, insertion of an expression control sequence or the essential portion thereof can be readily accomplished in production of vectors.

A fourth element, of course, is the DNA sequence coding for the desired product. As previously noted, this DNA sequence can be constructed synthetically, e.g., using the recognized phosphotriester method or other well-recognized methods.

Suitable cloning vectors can be used in a wide range of host organisms, for example, gram-negative prokaryotic organisms such as *Escherichia coli*, Serratia, Pseudomonas, and the like; gram-positive prokaryotic organisms, such as Bacillus, Streptomyces, and the like; and eukaryotic organisms, such as Saccharomyces, and the like. Preferably, the host organism is a gram-negative prokaryotic organism. Of gram-negative prokaryotic organisms, *E. coli* is especially preferred, for example, *E. coli* K-12 strains, such as RV308.

Employing well recognized methodology, the appropriately prepared cloning vectors are used to transform suitable host organisms, are amplified in such organisms, and protein product is expressed using standard fermentation conditions.

If the expression product is, as hereinbefore described, a hybrid protein, the product first can be treated with an agent to cleave the extraneous (endogenous) material, leaving a compound of this invention. If, however, the product results from direct expression, it will differ from the material obtained by cleavage of the hybrid protein only in that it will contain a leading methionine resulting from initiation of expression. The added methionine normally will not prohibit use of the product for its tailored purpose, i.e., separation from impurities by immobilized metal ion affinity chromatography.

As noted, the compounds of this invention comprise a chelating peptide covalently linked to a biologically active polypeptide or protein. The linkage can be direct or indirect. If indirect, the linkage normally will include a suitably tailored selective cleavage site which will permit ready removal of the chelating peptide with production of the desired end product. Any of the aforedescribed amino acid residues or sequences, as well as others, are suitable to serve as selective cleavage site.

Since the chelating peptide is small, i.e., a di-, tri-, tetra-, or pentapeptide, it can be directly linked to the biologically active polypeptide or protein. In many instances, the chelating peptide may remain joined to the biologically active polypeptide or protein, and the resulting molecule will retain most or all of the activity of the non-linked biologically active polypeptide or protein. Nevertheless, the chelating peptide, if joined directly to the biologically active polypeptide or protein at the amino terminal of the latter, can be removed by Edman degradation which sequentially removes single N-terminal amino acids. The number of cycles of Edman degradation that are necessary, of course, will depend upon the length of the chelating peptides.

As is implicit from the above, the chelating peptide may be joined, whether directly or indirectly, to either end of the biologically active polypeptide or protein. It is preferred, however, that the chelating peptide be located at the amino-terminus of the biologically active polypeptide or protein.

Typical examples of biologically active polypeptides and proteins that can advantageously participate in the present discovery are insulin A-chain, insulin B-chain, proinsulin, growth hormone, insulin-like growth factors, glucagon, somatostatin, growth hormone releasing factor, and the like.

Resins useful for producing immobilized metal ion affinity chromatography (IMAC) columns are available commercially. Typical examples of resins derivatized with iminodiacetic acid (IDA) are Chelating Sepharose 6B (Pharmacia), Immobilized Iminodiacetic Acid I and II (Pierce), and Chelex 100 (Bio-Rad). In addition, Porath has immobilized tris(carboxymethyl)ethylenediamine (TED) on Sepharose 6B [J. Porath and B. Olin, *Biochemistry* 22, 1621-1630 (1983)] and used it to fractionate serum proteins. Other reports suggest that trisacryl GF2000 and silica can be derivatized with IDA, TED, or aspartic acid, and the resulting materials used in producing IMAC substances. [Small et al., *Affinity Chromatography and Biological Recognition*, Academic Press, Inc., 267-268 (1983); Vijayalakshmi, *Affinity Chromatography and Biological Recognition*, Academic Press, Inc., 269-273 (1983); and Moroux et al., *Affinity Chromatography and Biological Recognition*, Academic Press, Inc., 275-278 (1983)].

An essential portion of the process of this invention involves elution of the precursor of the biologically active polypeptide or protein from the IMAC column following its selective adsorption. Generally, either of two recognized elution methods can be employed. The pH of the buffer may be lowered or a displacing ligand may be added to the buffer. In the former, the lowered pH protonates the coordinating groups, e.g., the imidazole ring of the histidine, on the polypeptide or protein. The resulting protonated ligands are incapable of forming coordinate covalent bonds with the immobilized metal ions; the polypeptides and proteins containing these ligands thus are washed from the column using a low pH buffer.

Adding a displacing ligand to the buffer causes dissociation of the polypeptides and proteins from immobilized metal ions; this method is especially useful if the polypeptide or protein of interest cannot tolerate a low pH environment. The ligand competes for and displaces the polypeptide or protein at coordination sites of the metal ion if its affinity for the latter is greater than that of the bound polypeptide or protein. An example of such a displacing ligand is ethylene-diaminetetraacetic acid (EDTA). Certain ligands can achieve displacement even if their binding affinity is not substantially greater than that of the bound polypeptide or protein if they are present in a large excess relative to the bound polypeptide or protein. Examples of such ligands are glycine, histidine, ammonia, and the like.

The following examples are provided for the purpose of illustrating the present invention. They are not intended to be limiting on the scope thereof.

EXAMPLE 1—Preparation of IMAC Column

Metal-free chelating resins (Sepharose 6B IDA, Pharmacia; Sepharose 4B IDA and Sephadex G25 IDA, Pierce) are supplied as aqueous suspensions containing either ethanol or sodium azide as preservative. The preservative was removed by repeatedly (3-5 times) resuspending the resin in distilled water after spinning the preservative-containing suspension at slow speed on a centrifuge. A 75% slurry of the preservative-free resin was poured into a 1×10 cm Econo-Column, and the resin was washed with 3-5 column volumes of distilled water.

The column was loaded with the selected metal ion [Ni(II), Co(II), or Cu(II) by adding 1 ml aliquots of a 50 mM metal chloride or metal sulfate aqueous solution until approximately 75% of the column was saturated with colored metal ion. For example, for Ni(II), addition of 3 ml of a 50 mM NiCl$_2$ solution left the bottom 25% of the column metal-free and available for trapping any dissociated Ni(II). The metal ion-containing column was washed with distilled water followed by high pH buffer (100 mM sodium phosphate, 100 mM NaCl, pH 7.5) and then low pH buffer (100 mM sodium phosphate, 100 mM NaCl, pH 4.3). The column then was fitted with a flow adaptor and equilibrated with high pH buffer using a peristaltic pump.

EXAMPLE 2—Binding and Elution of Histidine-Containing Peptides

Stock solutions of several histidine-containing di- and tripeptides were prepared at approximately 1 mg/ml concentration in high pH buffer. A 200 μl aliquot of each stock solution was separately pumped onto a metal ion affinity chromatography column using a peristaltic pump. The column then was washed with high pH buffer until all unbound material had eluted or, in those cases in which sample had bound to the column, until 10 column volumes of the buffer had passed through the column. The column then was washed with low pH buffer until all bound material had eluted. The column effluent was monitored at 210 nm using a Buchler Fracto-Scan monitor; fractions of 50 drops each (about 1.6 ml) were collected using a Gilson fraction collector. The pH of each fraction was measured, and Table I following lists the pH at which each histidine-containing small peptide eluted from each of three immobilized metal ion columns. An elution pH of 7.5 indicates an absence of binding to the particular immobilized metal ion.

TABLE I

| Peptide | Elution pH | | |
|---|---|---|---|
| | Ni(II) | Co(II) | Cu(II) |
| Gly-His | 5.9 | 7.5 | 7.5 |
| Gly-His-Gly | 7.5 | 7.5 | 7.5 |
| Gly-Gly-His | 7.5 | 7.5 | 7.5 |
| His-Gly | 5.4 | 7.5 | 4.5 |
| His-GlyNH$_2$ | 7.5 | 7.5 | 4.6 |
| His-Gly-His | 4.8 | 5.9 | 4.4 |
| Ala-His | 5.8 | 7.5 | 7.5 |
| His-Ala | 7.5 | 7.5 | 4.6 |
| His-Val | 5.4 | 7.5 | 4.4 |
| Leu-His | 7.5 | 7.5 | 7.5 |
| His-Leu | 5.4 | 7.5 | 4.5 |
| His-Ser | 5.4 | 7.5 | 4.5 |
| His-Glu | 7.5 | 7.5 | 4.6 |
| His-Lys | 5.4 | 7.5 | 4.6 |
| His-Phe | 5.2 | 7.5 | 4.5 |
| Tyr-His | 5.7 | 7.5 | 7.5 |
| His-Tyr | 5.2 | 7.5 | 4.4 |
| His-TyrNH$_2$ | 4.7 | 6.4 | 4.4 |
| His-Trp | 4.9 | 6.4 | 4.4 |
| Met-His | 7.5 | 7.5 | 7.5 |
| His-Met | 5.3 | 7.5 | 4.6 |

EXAMPLE 3—Binding Characteristics of Miscellaneous Proteins

Using a Ni(II) column prepared as described in Example 1 and the Methods described in Example 2, the following proteins were individually examined:
  A. Bovine Serum Albumin
  B. Carbonic Anhydrase
  C. Carboxypeptides A
  D. Cathepsin D
  E. Ceruloplasmin
  F. Conalbumin G. Cytochrome c
H. Ferritin
I. γ Globulin
J. Insulin (porcine)
K. Ovalbumin
L. Pancreatic Trypsin Inhibitor
M. Thyroglobulin
N. Transferrin
O. Tyrosinase
P. Bovine Pancreatic Polypeptide
Q. Chymotrypsinogen A
R. Met-Growth Hormone
S. Insulin A-chain (carboxymethylated)
T. Insulin B-Chain (carboxymethylated)
U. Myoglobin
V. Proinsulin
W. Superoxide Dismutase
X. Yeast Lysate None of the foregoing proteins exhibited any binding to the immobilized Ni(II) affinity chromatography column.

EXAMPLE 4—Comparison of Binding and Elution Characteristics of Four Similar Peptides The following four peptides were individually examined using the aforedescribed Ni(II) column:
A. p-Glu-His-Trp-Ser-Tyr-Gly-Leu-Arg-Pro-GlyNH$_2$
B. His-Trp-Ser-Tyr-Gly-Leu-Arg-Pro-GlyNH$_2$
C. Trp-Ser-Tyr-Gly-Leu-Arg-Pro-GlyNH$_2$
D. Ser-Tyr-Gly-Leu-Arg-Pro-GlyNH$_2$ Peptides A, C, and D each failed to bind to the immobilized Ni(II). Peptide B, containing the N-terminal His-Trp chelating peptide bound tightly and was eluted from the column at pH 4.7 using the low pH buffer.

EXAMPLE 5—Separation of Chelating Peptide from a Complex mixture of Chelating Peptide and Other Peptides and Proteins A protein and peptide mixture was prepared by mixing 100 μl of each protein stock solution (approximately 1 mg/ml) with 30 μl of each peptide stock solution (approximately 1 mg/ml). The proteins represented in the resulting mixture are those designated A-O in Example 3. The peptides represented are the following: Gly-His-Gly; His-Ala; His-Glu; Met-His; Gly-Gly-His; Leu-His; and His-Gly-NH$_2$.

An aliquot (about 500 μl) of the complex protein-peptide mixture was added to 100 μl of His-Trp stock solution. The mixture was treated on a Ni(II) Sephadex G25 IDA column prepared as described in Example 1 and under the conditions described in Example 2. Fractions of 1.6 ml each were collected. The proteins were completely eluted at pH 7.5 before Fraction 10, and the non-chelating peptides eluted at about Fractions 10–13. In contrast, His-Trp remained on the column; elution of His-Trp was effected at about Fractions 70–75 after the pH of the eluant was lowered using the pH 4.3 buffer beginning at about Fraction 65.

EXAMPLE 6—Separation of a Polypeptide Covalently linked to Chelating Peptide from a Complex mixture of Such Polypeptide and Other Peptides and Proteins A mixture was prepared using the method described in Example 5. The mixture contained the polypeptide His-Trp-Ser-Tyr-Gly-Leu-Arg-Pro-Gly-NH$_2$, proteins designated A-F, H, I, K, and M-O in Example 3 and metallotheinine, and the peptides (1) Gly-His-Gly; (2) His-Ala; (3) His-Glu; (4) Met-His; (5) Gly-Gly-His; (6) Leu-His; (7) His-Gly-NH$_2$; (8) Ala-His; (9) His-Lys; (10) His-Met; (11) Tyr-His; (12) His-Tyr; (13) His-Val; (14) His-Ser; (15) His-Leu; (16) His-Gly; (17) His-Phe; and (18) Gly-His.

The mixture was separated in accordance with the method and conditions described in Example 5. Under these conditions, the proteins and peptides 1–7 eluted before Fraction 20. The pH was lowered beginning at Fraction 50. Peptides 8–18 eluted at about Fractions 50–55, and the polypeptide of choice, containing the His-Trp terminal chelating peptide eluted alone at about Fractions 58–67.

EXAMPLE 7—Separation of a Polypeptide Covalently Linked to Chelating Peptide from a Mixture of Structurally Related Peptides A mixture of the following peptides was prepared using the method described in Example 5.
(1) His-Trp-Ser-Tyr-Gly-Leu-Arg-Pro-GlyNH$_2$
(2) Trp-Ser-Tyr-Gly-Leu-Arg-Pro-GlyNH$_2$
(3) Ser-Tyr-Gly-Leu-Arg-Pro-GlyNH$_2$ The mixture was separated in accordance with the method and conditions described in Example 5. Peptide 3 eluted at about Fractions 5–10 and peptide 2 at about Fractions 11–20. The pH was lowered beginning at about Fraction 40, and peptide 1, containing the chelating peptide, eluted at about Fractions 47–54.

We claim:

1. A compound comprising a biologically active polypeptide or protein covalently linked directly or indirectly to an immobilized metal ion chelating peptide.

2. Compound of claim 1, in which the immobilized metal ion chelating peptide has from 2 to about 5 amino acids.

3. Compound of claim 2, in which the immobilized metal ion chelating peptide contains at least one amino acid selected from the group consisting of histidine and cysteine.

4. Compound of claim 3, in which at least one amino acid of the immobilized metal ion chelating peptide is histidine.

5. Compound of claim 4 in which the immobilized metal ion chelating peptide has the formula His-X in which X is selected from the group consisting of -Gly-His, -Tyr, -Gly, -Trp, -Val, -Leu, -Ser, -Lys, -Phe, -Met, -Ala, -Glu, -Ile, -Thr, -Asp, -Asn, -Gln, -Arg, -Cys, and -Pro.

6. Compound of claim 5, in which X is selected from the group consisting of -Trp, -Tyr, -Gly-His, and -Phe.

7. Compound of claim 6, in which X is selected from the group consisting of -Trp, -Tyr, and -Gly-His.

8. Compound of claim 4, in which the immobilized metal ion chelating peptide has the formula Y-His in which Y is selected from the group consisting of -Gly, -Ala, and -Tyr.

9. Compound of claim 1, in which the immobilized metal ion chelating peptide is convalently linked directly or indirectly to the biologically active polypeptide or protein at the amino terminus of the latter.

10. Compound of claim 9, in which the immobilized metal ion chelating peptide is covalently linked indirectly via a selective cleavage site to the biologically active polypeptide or protein at the amino terminus of the latter.

11. Compound of claim 1, in which the immobilized metal ion chelating peptide chelates nickel (II) ion.

12. Compound of claim 1, in which the biologically active polypeptide or protein has the amino acid sequence of an insulin A-chain, an insulin B-chain, a proinsulin, or a growth hormone.

13. Process for separating a biologically active polypeptide or protein in the form of its precursor from a mixture containing said precursor and impurities, which comprises contacting said precursor with a resin containing immobilized metal ions, said precursor comprising the biologically active polypeptide or protein covalently linked directly or indirectly to an immobilized metal ion chelating peptide, binding said precursor to said resin, and selectively eluting said precursor from said resin.

14. Process of claim 12, in which the immobilized metal ion chelating peptide has from 2 to about 5 amino acids.

15. Process of claim 14, in which the immobilized metal ion chelating peptide contains at least one amino acid selected from the group consisting of histidine and cysteine.

16. Process of claim 15, in which at least one amino acid of the immobilized metal ion chelating peptide is histidine.

17. Process of claim 16, in which the immobilized metal ion chelating peptide has the formula His-X in which X is selected from the group consisting of -Gly-His, -Tyr, -Gly, -Trp, -Val, -Leu, -Ser, -Lys, -Phe, -Met, -Ala, -Glu, -Ile, -Thr, -Asp, -Asn, -Gln, -Arg, -Cys, and -Pro.

18. Process of claim 17, in which X is selected from the group consisting of -Trp, -Tyr, -Gly-His, and -Phe.

19. Process of claim 18, in which X is selected from the group consisting of -Trp, -Tyr, and -Gly-His.

20. Process of claim 16, in which the immobilized metal ion chelating peptide has the formula Y-His in which Y is selected from the group consisting of -Gly, -Ala, and -Tyr.

21. Process of claim 13, in which the immobilized metal ion chelating peptide is covalently linked directly or indirectly to the biologically active polypeptide or protein at the amino terminus of the latter.

22. Process of claim 21, in which the immobilized metal ion chelating peptide is covalently linked indirectly via a selective cleavage site to the biologically active polypeptide or protein at the amino terminus of the latter.

23. Process of claim 13, in which the biologically active polypeptide or protein has the amino acid sequence of an insulin A-chain, an insulin B-chain, a proinsulin, or a growth hormone.

24. Process of claim 13, in which the resin containing immobilized metal ions is selected from the group consisting of chelating Sepharose 6B, Immobilized Iminodiacetic Acid I, Immobilized Iminodiacetic Acid II, and Chelex 100.

25. Process of claim 13, in which the immobilized metal ion is the divalent ion of metals selected from the group consisting of cobalt, nickel, and copper.

26. Process of claim 25, in which the immobilized metal ion is the divalent ion of metals selected from the group consisting of nickel and copper.

27. Process of claim 26, in which the immobilized metal ion is nickel (II).

* * * * *